United States Patent [19]

Eckerle

[11] Patent Number: 4,799,491
[45] Date of Patent: Jan. 24, 1989

[54] BLOOD PRESSURE MONITORING METHOD AND APPARATUS

[75] Inventor: Joseph S. Eckerle, Redwood City, Calif.

[73] Assignee: SRI International, Menlo Park, Calif.

[21] Appl. No.: 927,843

[22] Filed: Nov. 6, 1986

[51] Int. Cl.⁴ .............................................. A61B 5/02
[52] U.S. Cl. ..................................... 128/672; 128/690
[58] Field of Search ...................... 128/672, 677–683, 128/687–690; 73/4 R

[56] References Cited

U.S. PATENT DOCUMENTS

| | | | |
|---|---|---|---|
| 3,123,068 | 3/1964 | Bigliano | 128/2.05 |
| 3,219,035 | 11/1965 | Pressman et al. | 128/2.05 |
| 3,880,145 | 4/1975 | Blick | 128/2.05 |
| 4,232,682 | 11/1980 | Veth | 128/671 |
| 4,262,675 | 4/1981 | Kubo et al. | 128/680 |
| 4,269,193 | 5/1981 | Eckerle | 128/672 |
| 4,271,843 | 6/1981 | Flynn | 128/681 |
| 4,408,614 | 10/1983 | Weaver et al. | 128/680 |
| 4,423,738 | 1/1984 | Newgard | 128/672 |
| 4,461,266 | 7/1984 | Hood, Jr. et al. | 128/680 |
| 4,519,401 | 5/1985 | Ko et al. | 128/748 |
| 4,597,393 | 7/1986 | Yamakoshi et al. | 128/677 |
| 4,638,810 | 1/1987 | Ramsey, III et al. | 128/681 |
| 4,646,749 | 3/1987 | Berger et al. | 128/687 |
| 4,649,929 | 3/1987 | Weaver et al. | 128/680 |
| 4,660,566 | 4/1987 | Palti | 128/677 |
| 4,669,485 | 6/1987 | Russell | 128/679 |

OTHER PUBLICATIONS

Pressman, G.L. et al., "A Transducer for the Continuous External Measurement of Blood Pressure", IEEE Trans. Bio–Med. Elec., Apr. 1963, pp. 73–81.

Primary Examiner—Francis Jaworski
Assistant Examiner—George Manuel
Attorney, Agent, or Firm—Victor R. Beckman

[57] ABSTRACT

Intraarterial blood pressure is measured noninvasively by an electromechanical transducer. The correct hold-down force to be applied to the transducer for obtaining accurate blood pressure measurements is determined by obtaining a set of at least one of the diastolic pressure, systolic pressure, and pulse amplitude versus hold-down pressure values over a range of hold-down pressures between which the underlying artery is unflattened and it is occluded. A polynomial is fitted to at least one of the sets of values, from which polynomial the correct hold-down pressure is determined. The hold-down pressure at the point of minimum slope of graphs of the polynominals fitted to the systolic and diastolic versus hold-down pressure values provides an indication of the correct hold-down pressure. An indication of the correct hold-down pressure using the pulse amplitude measurements is provided by locating the midpoint of a pair of hold-down pressures at which the pulse amplitude is substantially sixty percent of the maximum pulse amplitude on the graph of the polynomial fitted to the pulse amplitude versus hold-down pressure values. An alternative method determines the correct hold-down pressure directly from the pulse-amplitude polynomial coefficients. A measure of the compliance of the underlying artery is obtained from the ratio of the minimum slope of the graph of the polynomial fitted to one of the systolic and diastolic versus hold-down pressure values to the slope of a straight line fitted to a subset of one of the systolic and diastolic versus hold-down pressure values over a range of hold-down pressures below which flattening of the underlying artery occurs.

20 Claims, 6 Drawing Sheets

BLOOD PRESSURE MONITORING METHOD AND APPARATUS

ORIGIN OF THE INVENTION

The invention described herein was made in the course of work under a grant or award from the Department of Health and Human Services.

TECHNICAL FIELD

This invention relates to method and apparatus for non-invasively monitoring blood pressure through use of a transducer array of individual pressure or force sensing elements, and to method and means for ascertaining the correct transducer hold-down pressure required for obtaining accurate blood pressure measurements.

BACKGROUND OF THE INVENTION

The continuous measurement of blood pressure by use of arterial tonometer transducers is well known as shown in U.S. Pat. Nos. 3,123,068 to R. P. Bigliano, 3,219,053 to G. L. Pressman, P. M. Newgard and John J. Eige, 3,880,145 to E. F. Blick, 4,269,193 to the present inventor, and 4,423,738 to P. M. Newgard, and in an article by G. L. Pressman and P. M. Newgard entitled "A Transducer for the Continuous External Measurement of Arterial Blood Pressure" (IEEE Trans. Bio-Med. Elec., April 1963, pp. 73-81).

In a typical tonometric technique for monitoring blood pressure, a transducer which includes an array of pressure sensitive elements is positioned over a superficial artery, and a hold-down force is applied to the transducer so as to flatten the wall of the underlying artery without occluding the artery. The pressure sensitive elements in the array typically have at least one dimension smaller than the lumen of the underlying artery in which blood pressure is measured, and the transducer is positioned such that at least one of the individual pressure-sensitive elements is over at least a portion of the underlying artery. The output from one of the pressure sensitive elements is selected for monitoring blood pressure. In some prior art arrangements, the pressure sensitive element having the maximum pulse amplitude output is selected, and in other arrangements the element having a local minimum of diastolic or systolic pressure which element is within substantially one artery diameter of the element which generates the waveform of maximum pulse amplitude is selected.

The pressure measured by the selected pressure sensitive element, i.e. the element centered over the artery, will depend upon the hold-down pressure used to press the transducer against the skin of the subject. Although fairly accurate blood pressure measurements are obtained when a hold-down pressure within a rather wide pressure range is employed, it has been found that there exists a substantially unique value of hold-down pressure within said range for which tonometric measurements are most accurate. This so-called "correct" hold down pressure varies among subjects. With prior art tonometric type transducers the correct hold-down pressure often is not determined thereby leading to inaccuracies in the blood pressure measurements.

SUMMARY AND OBJECTS OF THE INVENTION

An object of this invention is the provision of an improved tonometric type method and apparatus for non-invasively monitoring blood pressure with a high degree of accuracy.

Another object of this invention is the provision of such a blood pressure measuring method and apparatus which includes the use of a transducer having an array of individual arterial riders (pressure sensitive elements) and wherein means are provided for determining the correct pressure required to hold the transducer against the subject to assure accuracy of the blood pressure readings.

The present invention includes a transducer array for generation of electrical waveforms indicative of blood pressure in an artery. Using the selected pressure sensing element that is determined to be positioned substantially over the center of the underlying artery, a set of at least one of the diastolic pressure, systolic pressure, or pulse amplitude pressure versus hold-down pressure values over a range of hold-down pressures between which the underlying artery is unflattened and is occluded is obtained. A polynomial is fitted to at least one of the sets of values from which polynomial the correct hold-down pressure is determined. The hold-down pressure at the point of minimum slope of graphs of the polynomials fitted to the systolic or diastolic versus hold-down pressure values provides an indication of the correct hold-down pressure. An indication of the correct hold-down pressure using the pulse amplitude measurements is provided by locating the point where the slope of the polynomial is zero or the midpoint of a pair of hold-down pressures at which the pulse amplitude is substantially sixty percent of maximum pulse amplitude of the graph of the polynomial fitted to the pulse amplitude versus hold-down pressure values. A measure of compliance of the underlying artery is obtained from the ratio of the minimum slope of the graph of the polynomial fitted to one of the systolic or diastolic pressure versus hold-down pressure values to the slope of a straight line fitted to a subset of one of the systolic or diastolic versus hold-down pressure values over a range of hold-down pressure below which flattening of the underlying artery begins or it may be obtained directly from the polynomial coefficients. The hold-down pressure at which flattening of the underlying artery begins is taken as the lowest of the above-mentioned pair of hold-down pressures at which the pulse amplitude is substantially sixty percent of maximum pulse amplitude of the graph of the polynomial fitted to the pulse amplitude versus hold-down pressure values.

BRIEF DESCRIPTION OF THE DRAWINGS

The invention, together with the above and other objects and advantages thereof will be better understood from the following description when considered with the accompanying drawings. It will be understood, however, that the illustrated embodiments of the invention are by way of example only and that the invention is not limited thereto. The novel features which are believed to be characteristic of the invention are set forth with particularity in the appended claims. In the drawings, wherein like reference characters refer to the same parts in the several views:

Figure 1:
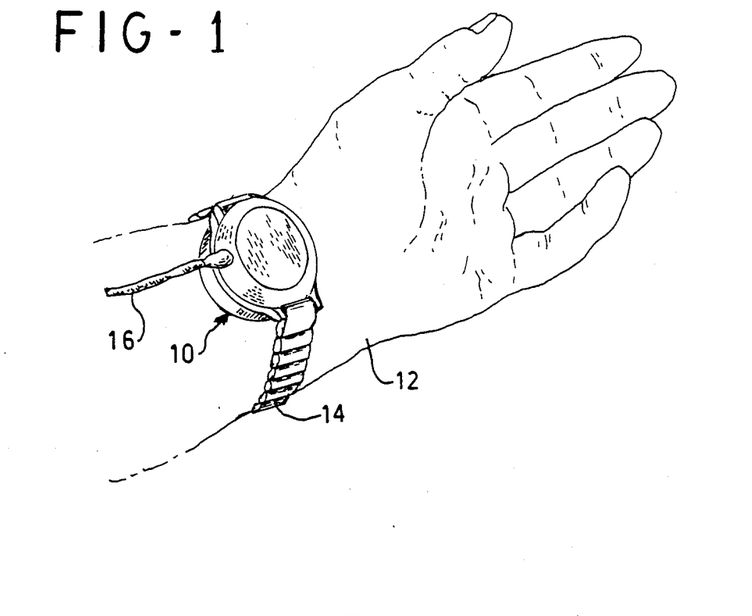
FIG. 1 shows the external appearance of a blood pressure transducer case, typically positioned over a superficial artery such as the radial artery, for providing a continuous external measurement of arterial blood pressure.
Figure 3:
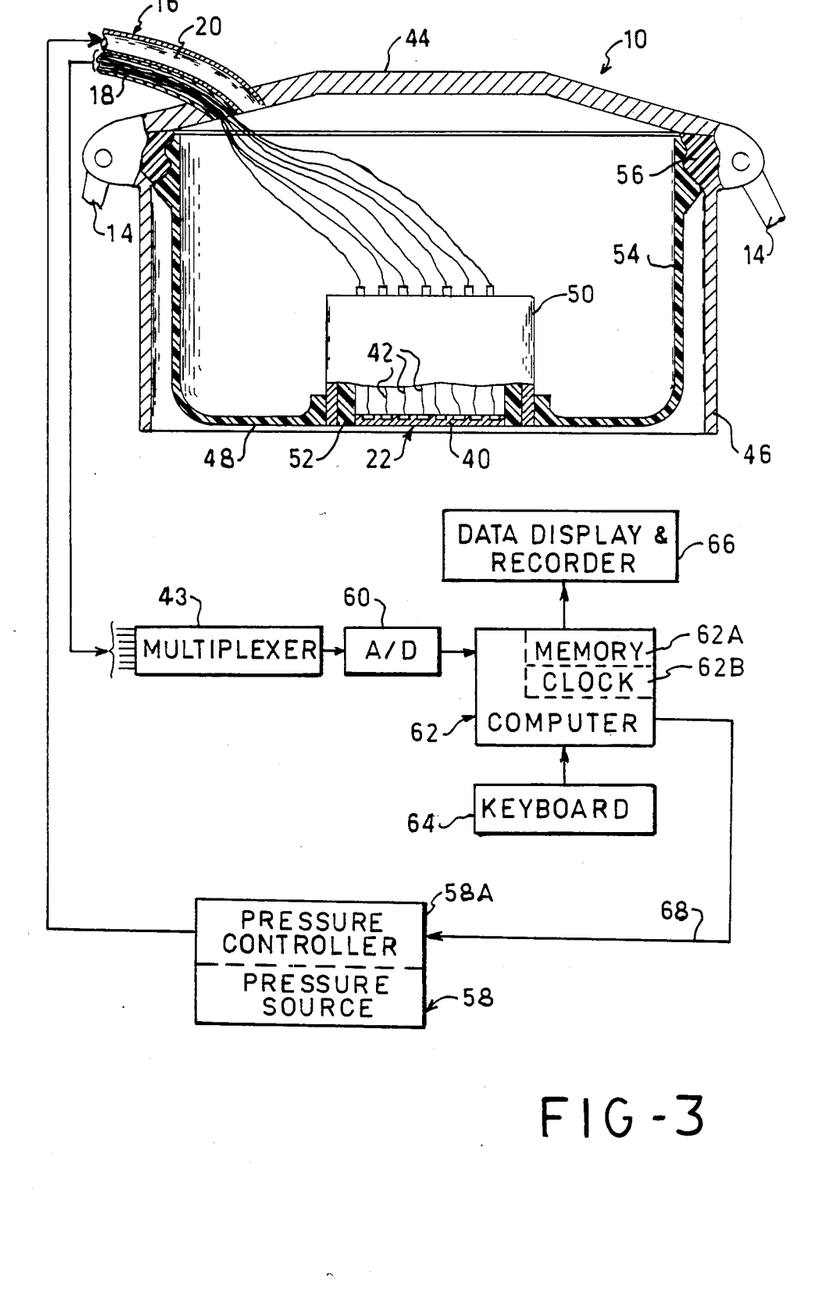
FIG. 3 is a combination simplified vertical sectional view taken through the transducer case of FIG. 1 and block diagram of a system which may be employed therewith in the practice of this invention.

A typical application of the transducer array for arterial tonometry is illustrated in FIG. 1 wherein the transducer housing, or case, 10 which may have the appearance of an ordinary wristwatch case, is held in place over the radial artery in a human wrist 12 by a band 14. A cord 16 extends from the transducer housing 10 through which electrical wiring for the transducer array within the housing, together with a small tube that connects the housing to an air pressure source, extend. The wiring 18 and tube 20 are shown in FIG. 3, but not in FIG. 1.

Figure 2:
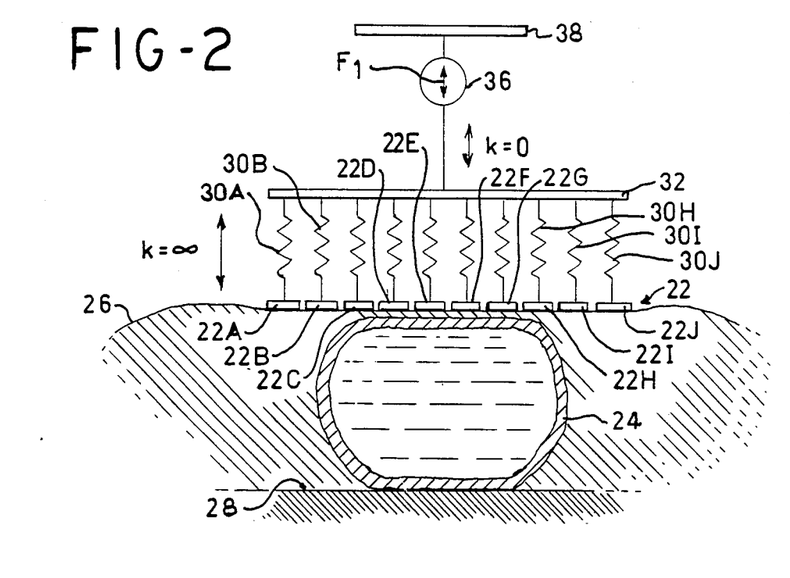
FIG. 2 is a schematic diagram illustrating the force balance between the artery and the multiple transducer elements (arterial riders), with the artery wall properly depressed to give accurate blood pressure readings.

Reference now is made to FIG. 2 wherein a diagrammatic mechanical model is shown which is representative of factors to be considered in the physical system. The illustrated model is that shown in the above-mentioned J. S. Eckerle U.S. Pat. No. 4,269,193 which was adapted from the G. L. Pressman and P. M. Newgard article entitled "A Transducer for the Continuous External Measurement of Arterial Blood Pressure". In brief, an array 22 of individual pressure sensitive elements or transducers 22A through 22J which constitute the arterial riders, is positioned so that one or more of the riders are entirely over an artery 24. The individual riders 22A-22J are small relative to the diameter of the artery 24 thus assuring that at least one of the riders in its entirety is over the artery. The skin surface 26 and artery underlying the transducer must be flattened by application of a hold-down pressure to the transducer. One rider overlying the center of the artery is identified as the "centered" arterial rider, from which arterial rider pressure readings for monitoring blood pressure are obtained. Means for selecting the arterial rider are disclosed in the above-mentioned J. S. Eckerle patent and G. L. Pressman and P. M. Newgard article. Using the above-mentioned rider selecting means, rider 22E, for example, may be selected as the "centered" arterial rider, in which case the remainder of the riders, here riders 22A-22D and 22F through 22J comprise side plates which serve to flatten the underlying skin and artery. Depending upon the positioning of the transducer on the subject, a different transducer element may be positioned over the center of the artery and thereby be selected as the "centered" arterial rider.

Superficial arteries, such as the radial artery, are supported from below by bone which, in FIG. 2 is illustrated by ground symbol 28 under the artery. The wall of artery 24 behaves substantially like a membrane in that it transmits tension forces but not bending moments. The artery wall responds to the loading force of the transducer, and during blood pressure measurements acts as if it is resting on the firm base 28. The effective stiffness of an artery wall is small and differs between subjects. In prior art mechanical models of the physical system, the effective stiffness of the artery wall is taken as zero, in which case the actual hold-down pressure employed is not considered to affect accuracy of the blood pressure readings so long as the transducer is pressed against the skin surface with sufficient force to cause compression but not occlusion of the underlying artery. Applicant has found that not only are blood pressure readings dependent upon hold-down pressure within the range of hold-down pressures that the artery is flattened but not occluded, but that most accurate blood pressure readings are obtained where a hold-down pressure is selected that is substantially midway between the pressure where flattening of the artery begins and the minimum pressure required for occluding the same. Novel steps involved in computing the correct hold-down pressure are described in detail hereinbelow following completion of the description of the mechanical model of FIG. 2 and the overall system shown in FIG. 3.

With the illustrated system, the transducer case 10 and mounting strap 14 together with air pressure applied to a bellows, 54, supply the required compression force and hold the riders 22A-22J in such a manner that arterial pressure changes are transferred to the riders which overlie the artery 24. Diagrammatically this is illustrated by showing the individual riders 22A-22J backed by rider spring members 30A-30J, respectively, a rigid spring backing plate 32, and a hold-down force generator 36 between the backing plate 32 and the mounting strap system 38.

If, without force generator 36, the coupling between the mounting strap system 38 and spring backing plate 32 were infinitely stiff to restrain the riders 22A-22J rigidly with respect to the bone structure 28, the riders would be maintained in a fixed position relative to the artery. In practice, however, such a system is not practical, and hold-down force generator 36, comprising a pneumatic or other suitable loading system, is included to keep constant the force applied by the mounting strap system 38 to riders 22A through 22J. In the mechanical model the spring constant, k (force per unit of deflection) of the force generator 36 is nearly zero. Suitable pneumatic loading systems are shown and described in the above-referenced U.S. Pat. Nos. 3,219,035, 4,269,193 and the Pressman-Newgard IEEE article.

In order to insure that the riders 22A through 22J flatten the artery and provide a true blood pressure measurement, they must be rigidly mounted to the backing plate 32. Hence, the rider springs 30A through 30J of the omdel ideally are infinitely rigid (spring constant $k = \infty$). It is found that as long as the system operates in such a manner that it can be modeled by rider springs 30A through 30J having a spring constant on the order of about ten times the value for the artery-skin system, so that the deflection of riders 22A through 22J is small; a true blood pressure measurement may be obtained when the correct hold-down pressure is employed.

The actual physical structure of a practical transducer of a type which may be employed for transducer array 22 in the present system is shown in the above-mentioned J. S. Eckerle U.S. Pat. No. 4,269,193. There, a transducer array is shown in which the individual transducers (riders) are formed in a thin monocrystalline silicon substrate which is made using integrated circuit techniques. In FIG. 3, to which reference now is made, a simplified showing of transducer 22 is shown comprising a chip 40 which includes an array of individual tranducers, not shown. Electrical conductors 42 connect the individual transducers to the wiring 18 for connection thereof to a multiplexer 43.

As seen in FIG. 3, case 10 comprises a generally cylindrical, hollow, container having rigid back and side walls 44 and 46, rspectively. The silicon transducer chip 40 is mounted within the face 48 of the case (designated as the front or operative face) in a cylindrical cup-like transducer housing 50. The operative face 48 includes the silicon transducer chip 40 along with its included individual transducers and arterial riders. Chip 40 may be affixed to a conventional ceramic dual in-line package that is plugged into an associated dual in-line socket, neither of which are shown in the drawings. A silicone rubber filler 52 is provided inside the housing 50 and around the dual in-line package and socket to provide a good seal, prevent electrical leakage between the transducer circuits and housing 50, and provide a flat surface to press against the subject. The front face 48 of the transducer includes the lower faces of housing 50 and filler 52.

The transducer housing 50 is fixed to the inside of the transducer case 10 by means of a cup-like silicone rubber bellows 54 which is sealed around the lower outside lip of the cup-shaped transducer housing 50, extends upwardly inside the outer wall of the transducer case 10, and is sealed to a ring 56, which in turn is fixed and sealed to the inside back of the transducer case 10. A chamber is formed inside the bellows which is connected to an air pressure source 58 through tube 20. A pressure controller 58A may be included in the pressure source. Since the flexible bellows 54 is sealed both to the transducer housing 50 and the inside of the transducer case 10, air under pressure from source 58 pneumatically loads the operative face 48. With the transducer strapped to the subject's wrist, the hold-down force $F_1$ exerted by the transducer array against the skin of the subject is adjustable by control of the air pressure. (In the diagrammatic mechanical model shown in FIG. 2 the hold-down force $F_1$ is generated by hold-down force generator 36.)

As noted above, electrical signals related to pressure sensed by the individual transducers 22A–22J of transducer 22 are supplied as inputs to an analog multiplexer 43. From the multiplexer, the signals are digitized by an analog-to-digital (A-D) converter 60, and the digitized signals are supplied to a digital computer 62 having memory 62A and a clock 62B. Other information, such as the subjects name, sex, weight, height, age, arm/wrist dimensions, and the like, may be supplied to the computer through a keyboard 64. Output from the computer is supplied to data display and recorder means 66 which may include a recorder, cathode ray tube monitor, a solid state display, or the like. If desired, at least a portion of the visual display may be included in transducer case 10. In fact, all of the components shown in FIG. 3 may be included in the case 10 without departing from the principles of this invention. Obviously, the computer output may be supplied to a printer, an audible alarm, or the like, as desired. Also, an output from the computer is supplied over line 68 to the pressure controller for control of the transducer hold-down pressure.

Figure 4:
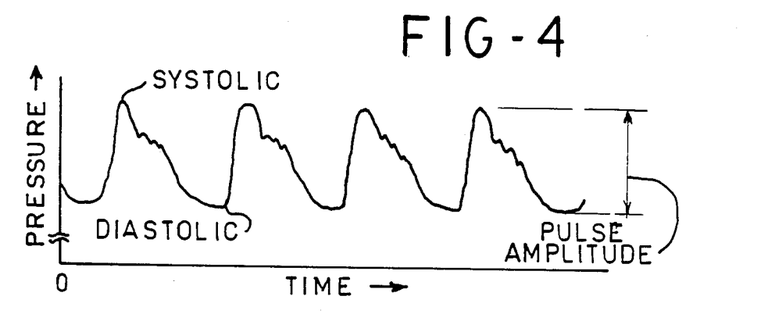
FIG. 4 is a waveform of human blood pressure versus time of the type which may be obtained using the present invention for illustrating systolic and diastolic pressure and pulse amplitude of the blood pressure wave.

In FIG. 4, to which reference now is made, the signal waveform of the output from one of the pressure sensitive elements 22A through 22J which overlies artery 24 is shown. Other elements of the transducer array which overlie the artery will have waveforms of similar shape. With a correct hold down pressure and correct selection of the "centered" arterial rider (i.e. the rider substantially centered over the artery) the waveform is representative of the subject's blood pressure within the underlying artery. Systolic, diastolic and pulse amplitude pressures are indicated on the waveform, wherein pulse amplitude is the difference between the systolic and diastolic pressures for a given heartbeat.

OVERALL SYSTEM OPERATION

Figure 5A:
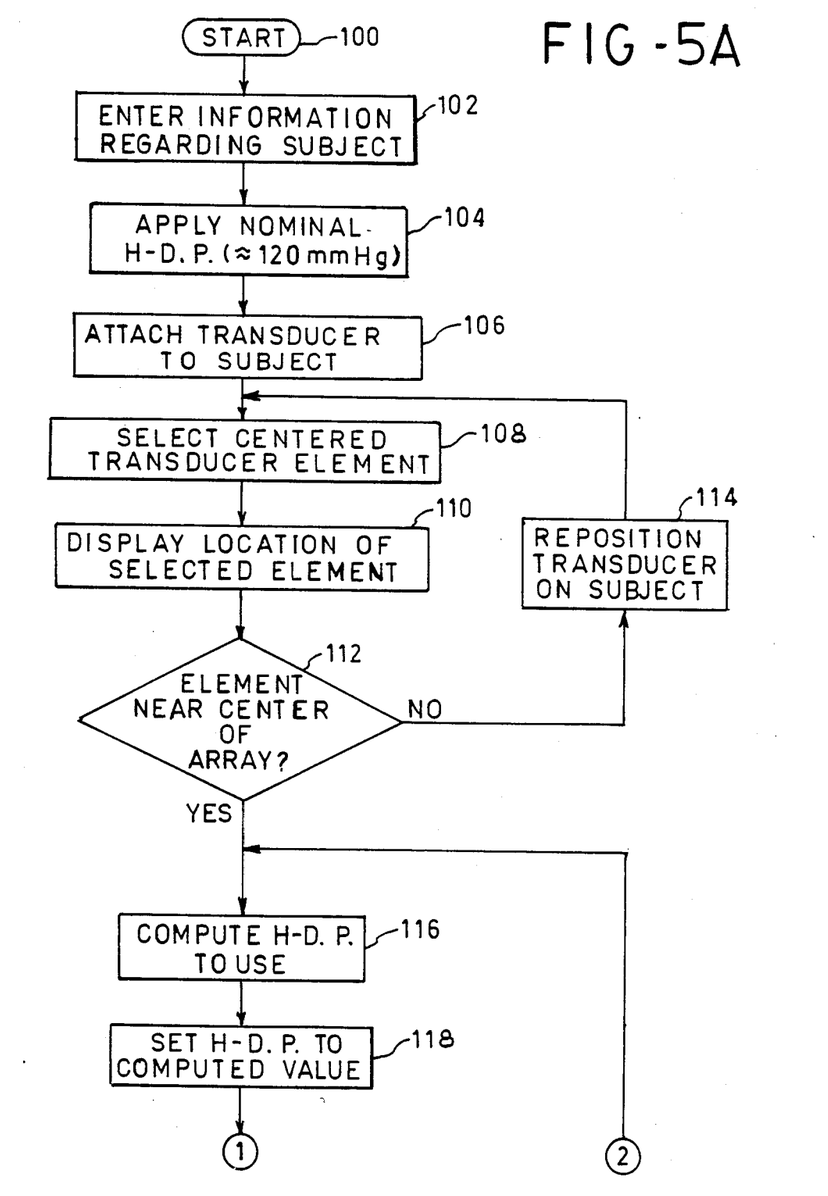
FIGS. 5A and 5B together show a flow chart for use in explaining overall operation of this invention.
Figure 5B:
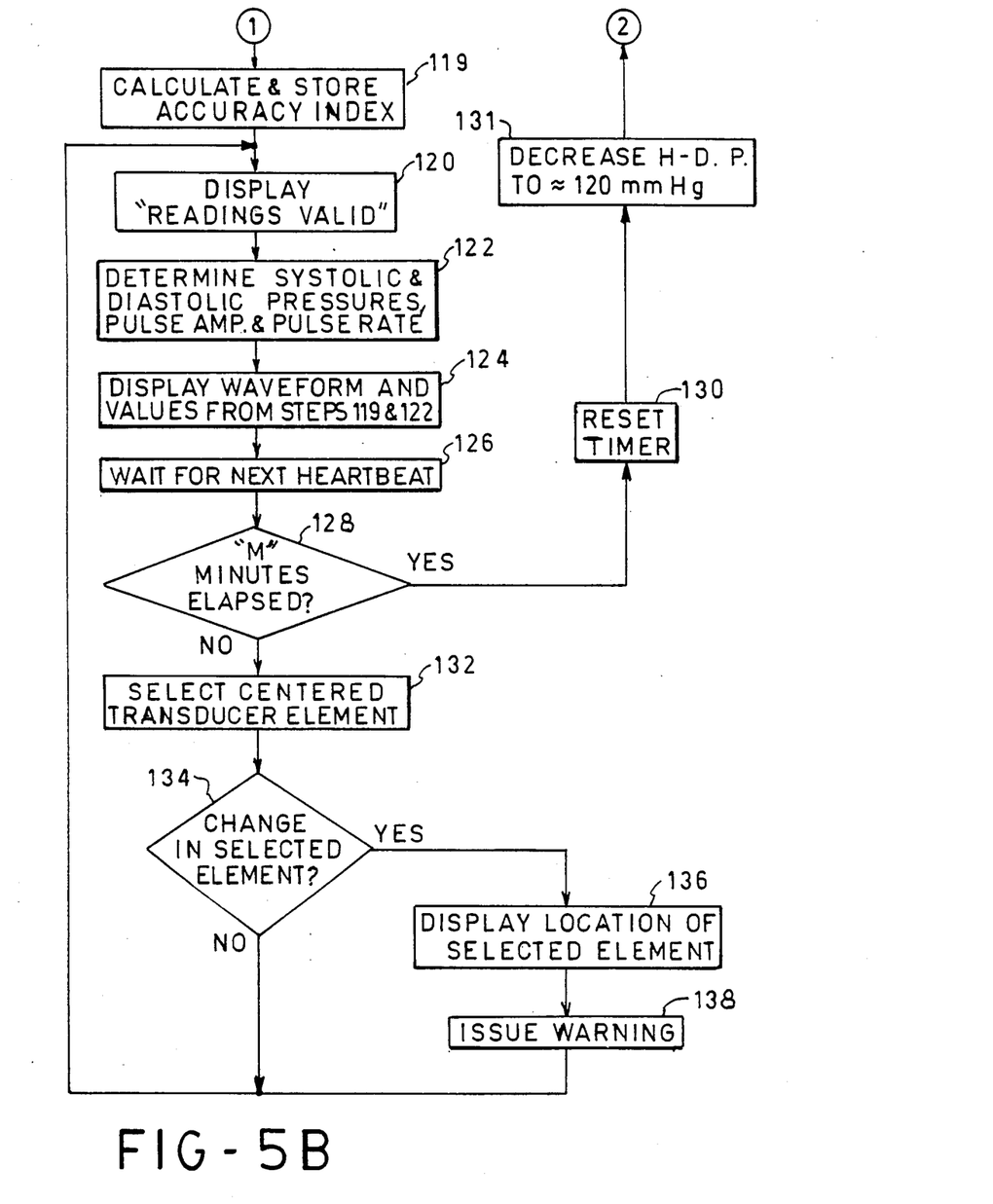

FIGS. 5A and 5B, together show a flow chart of an algorithm for general, overall, operation of the blood pressure monitoring system. Some of the operations indicated therein are under control of computer 62 responsive to programming instructions contained in memory unit 62A. Obviously, one or more programmable steps may be involved in the actual implementation of the indicated operations. Since the programming of such steps is well within the skill of the average programmer, a complete program listing is not required and is not included herein.

Preparation for monitoring is begun at START step 100 at which time system power is turned on or a reset operation is performed, by means not shown, and counters, registers, timers, and the like in computer 62 are initialized. At step 102 information concerning the subject, such as the subject's name, sex, weight, height, age, arm and/or wrist dimensions, and the like, is entered into the computer memory through use of the keyboard 64. Next, at step 104, a nominal hold-down pressure (H-D.P.) is applied wherein air under pressure from source 58 is supplied to the transducer. For example, a hold-down pressure of say 120 mmHg may be supplied to the transducer, which pressure serves to extend the bellows 54 whereby operative face 48 extends outwardly a short distance from the bottom of the case 10. The transducer is attached to the subject at step 106 at a location wherein a centrally located transducer element, such as element 22E of transducer array 22 overlies the center of artery 24. Of course, the exact position of the transducer array relative to the underlying artery generally is not visually apparent to the subject, or operator, and repositioning of the transducer may be required to properly position the same.

With the transducer attached to the subject, step 108 is entered (select centered transducer element) at which point the transducer element which overlies the center of the artery is identified. The location of the selected transducer element is displayed at step 110. If desired, the exact transducer element 22A through 22J selected at step 108 may be displayed at step 110. Alternatively, a linear array of, say, three lights may be provided wherein energization of the center light indicates that a centrally located transducer element was selected at step 108. Illumination of either of the end lights would indicate that movement of the transducer to the right or left is required for proper positioning of the transducer array relative to the underlying artery. As noted above, selection step 108 may include means for selecting the one pressure sensitive element that has a local minimum of at least one of the diastolic and systolic pressures that is within substantially one artery diameter of the one pressure sensitive element which generates the waveform of maximum pulse amplitude, as disclosed in U.S. Pat. No. 4,269,193. Processes which may be employed in selection step 108, including identifying systolic and diastolic pressures, pulse amplitude, maxima, local minimum, and the like, from the transducer outputs are readily implemented using digital computer 62.

After the transducer element directly over the artery is selected and its location displayed, decision step 112 is entered to determine whether or not the selected element is near the center of the transducer array. If it is not, the transducer is repositioned on the subject at step 114, and step 108 is reentered. The process is repeated until the transducer is properly located on the subject.

Figure 7:
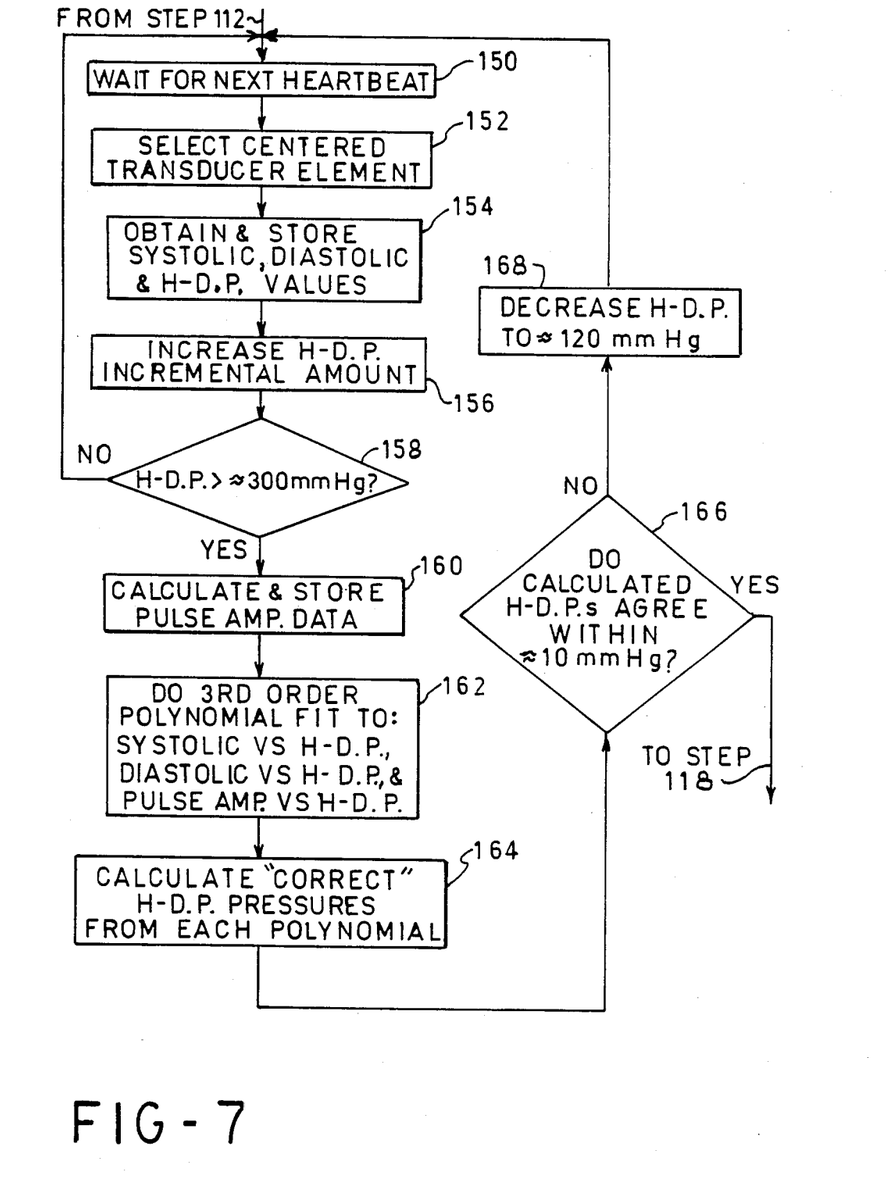
FIG. 7 is a flow chart showing details of the computation of a correct hold-down pressure.

When decision step 112 is affirmative, the hold-down pressure to use is computed at step 116. An affirmative decision at step 112 may require the operator to actuate an "Adjust Pressure" button, or the like, to enter step 116 fromn step 112. Novel algorithms which may be used in computing the correct hold-down pressure (step 116) are shown in FIG. 7 and described below. For present purposes it will be understood that a correct hold-down pressure for accurate blood pressure monitoring is computed at step 116, following which, at step 118, the computed hold-down pressure is set by control of pressure controller 58A by the computer 62.

Data obtained and used to compute the correct hold-down pressure (step 116 may be used in the calculation of an accuracy index at step 119, which index simply comprises a measure of the compliance of the underlying artery 24. Generally, the more compliant, or less stiff, the underlying artery, the better will be the accuracy of the blood pressure measurements. Means for computing the compliance and accuracy index are described in detail hereinbelow. For present purposes, it will be understood that the accuracy index may be caluculated at step 119 (FIG. 5B) and the value thereof stored for display at a later step with blood pressure measurements.

With the transducer properly positioned on the subject and the correct hold-down pressure supplied thereto, the system is in condition for obtaining accurate blood pressure readings. At step 120 an indication that the system is operative is provided, as by display of the words "Readings Valid". Obviously, other displays, such as a green indicator light, may be employed for indicating the operating state of the system.

From the output from the selected transducer element, systolic and diastolic pressure values together with pulse amplitude values are readily determined in step 122. Also, pulse rate is readily calculated by determining the time between successive diastolic or systolic pressures. At step 124, values calculated and determined in steps 119 and 122 are displayed and/or recorded along with the actual waveform. Obviously, the values which are calculated and displayed depend upon the use to be made of the blood pressure monitor, a display of all of the values not being required in many instances. For example, the blood pressure waveform could be recorded without calculation and display of any of the values identified in steps 119 and 122.

After the values identified in step 124, such as systolic and/or diastolic pressure, are displayed, step 126 is entered wherein the system waits for the next heartbeat cycle. Diastolic or systolic pressure points may be used to identify reference points in the heartbeat cycles. Decision step 128 then is entered at which time a timer in computer 62 is tested to determine whether or not it has reached a predetermined time "M", where M is a time period of, say, 30 minutes. If the elapsed time exceeds the predetermined time period, M, the decision is affirmative, the timer is reset at step 130, hold-down pressure is reduced to approximately 120 mmHg at step 131, and step 116 is reentered for recomputation of the correct hold-down pressure and resetting thereof, if required. Periodic checking and resetting of hold-down presure helps to assure long-term accuracy of the blood-pressure readings.

If the predetermined time period has not been exceeded, step 132 is entered for selection of the central transducer element, which step is the same as step 108 described above. Decision step 134 then is entered in which the selected transducer element determined in step 108 is compared to that determined in step 132. If there is no change in the selected transducer element, step 120 is reentered indicating that the readings are valid. However, if there has been a change in the selected transducer element, such that decision step 134 is affirmative, then step 136 is entered wherein the newly-determined selected transducer is displayed. This step corresponds to step 110 wherein either the actual selected transducer element is identified, or arrows or lights indicate the direction that the transducer needs to be moved to recenter the same over the underlying artery. A warning is issued at step 138 indicating to the subject or operator that movement of the transducer relative to the artery has taken place. If desired, the transducer then may be repositioned and the process restarted. If the transducer is not repositioned, and the process is not terminated and restarted, step 120 is reentered for continuation of the monitoring process, but now using the output from the newly selected transducer element.

Figure 6:
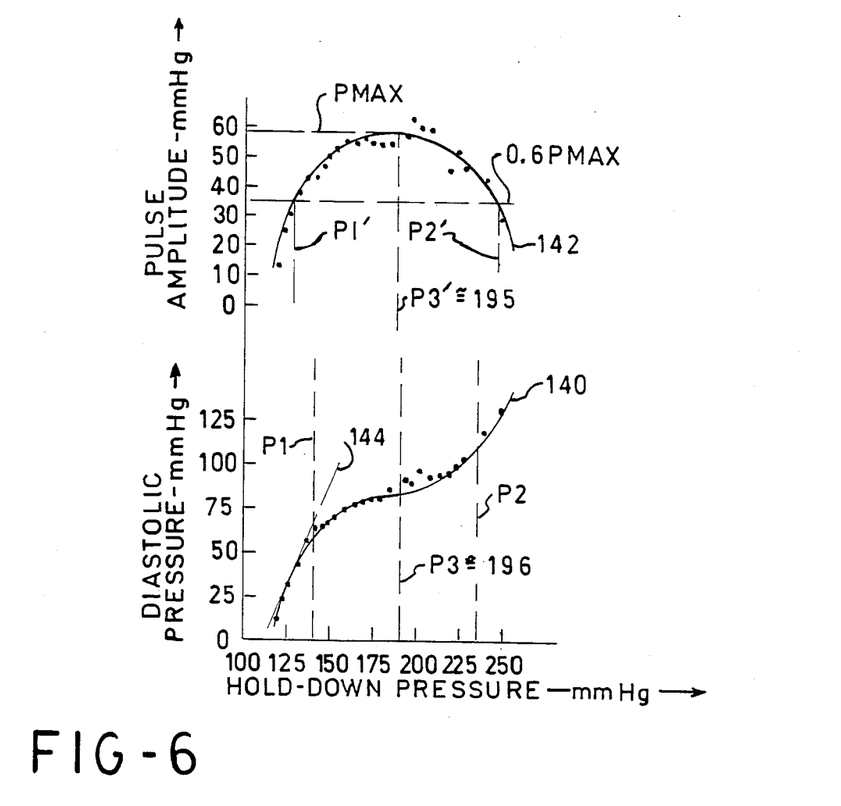
FIG. 6 shows plots of diastolic pressure and pulse amplitude versus hold-down pressure for a typical subject.

DETERMINATION OF HOLD-DOWN PRESSURE (1) Diastolic pressure vs Hold-Down Pressure Method Reference is made to FIG. 6 wherein plots of diastolic pressure and pulse amplitude versus hold-down pressure are shown which will facilitate an understanding of novel means for determining correct hold-down pressure for accurate blood pressure mesurements. The method for obtaining the data points in this plot will be described below. A third-order polynomial is fitted using, for example, least squares techniques to the FIG. 6 series of diastolic pressure points to provide a curve 140 which has the typical shape shown regardless of physical characteristics of the subject.

A third-order polynomial fitted to the measured data may be written as follows:

$$P_m = a_0 + a_1 P_h + a_2 P_h^2 + a_3 P_h^3 \qquad (1)$$

wherein:
$P_m$ = measured diastolic pressure,
$P_h$ = hold-down pressure, and
$a_0$, $a_1$, $a_2$, and $a_3$ are coefficients of the polynomial.

For hold-down pressures between zero and P1, the underlying artery remains unflattened, and the measured pressure is primarily dependent upon the hold-down pressure and secondarily upon the intraarterial pressure, Pa. The graph of the polynomial is a relatively straight line over this range. Up to pressure P1 the effective spring constant of the artery, using the mechanical model of the system shown in FIG. 2, is large.

Between hold-down pressures P1 and P2 the hold-down pressure is great enough to partially flatten the underlying artery, but not great enough to occlude it. Experiment has shown that most accurate blood pressure measurements are obtained when a hold-down pressure that is substantially midway between pressures P1 and P2 is employed. Between pressures P1 and P2 the effective spring constant of the artery using the mechanical model of FIG. 2, is relatively small.

At hold-down pressures greater than P2, the underlying artery is completely occluded, and the effective spring constant of the underlying artery is again relatively large. Consequently, the measured pressure is again substantially independent of the intraarterial pressure, Pa, and the curve is substantially a straight line above pressure P2. As seen in FIG. 6, the slope of curve 140 is lowest between pressures P1 and P2 where the underlying artery is flattened but not occluded. As noted above, substantially the center, or midpoint, of this region of lowest slope, between P1 and P2, is the correct hold-down pressure for obtaining accurate blood pressure measurements. This midpoint also substantially conicides with the point where the slope of the graph of the polynomial (equation 1) is minimum. Therefore, the correct hold-down pressure value is readily determined by locating the minimum slope point using coefficients of the graph 140 of the polynomial fitted to the diastolic pressure points. In particular:

$$P3 = -a_2/3a_3 \quad (2)$$

where: P3, the point of miminum slope, is the correct hold down pressure, and $a_2$ and $a_3$ are the coefficients of the second and third degree terms of the third-order polynomial.

For curve 140 of FIG. 6, $a_2 = -0.084760$ and $a_3 = 0.00014431$ whereby, from equation (1) a correct hold-down pressure of approximately 196 mmHg is indicated.

(2) Systolic Pressure vs Hold-Down Pressure Method

Instead of using a plot of diastolic pressure vs hold-down pressure to determine the correct hold-down pressure, a plot of systolic pressure versus hold-down pressure points may be employed. The method is the same as that described above except that a third order polynomial is fitted to the series of systolic pressure points, and equation (2) is applied to the resultant polynomial to provide an indication of the correct hold-down pressure.

(3) Pulse Amplitude vs Hold-Down Pressure Method

A. A third method of determining the correct hold-down pressure to use in monitoring blood pressure involves the use of the plot of pulse amplitude vs hold-down pressure points shown in FIG. 6. As with the plot of diastolic pressure vs hold-down pressure, a third order polynomial is fitted to the series of pulse amplitude points which results in a generally inverted U-shaped curve 142. It has been found that values of hold-down pressure corresponding roughly to pressures P1 and P2 shown in FIG. 6 may be found by taking the pressures where the pulse amplitude is 0.6 times the maximum pulse amplitude on the graph of polynomial, 142. In FIG. 6, these 0.6 maximum hold-down pressure points are identified as P1' and P2'. The correct hold-down pressure, P3', is the value substantially midway between these points. Using this method, the correct hold-down pressure is $$P3' = (P1' + P2')/2 \quad (3)$$

For curve 142 of FIG. 6 a correct hold-down pressure of approximately 195 mmHg is indicated by Eq. (3). For the subject from which the diastolic and pulse amplitude plots of FIG. 6 were obtained, the correct hold-down pressure determined using equations (2) and (3) differ by only one mmHg. If "correct" hold-down pressure values calculated using the three above-described methods agree within approximately 10 mmHg, then substantially correct blood pressure measurements are obtained using any one of said calculated values.

B. In a variation of the pulse amplitude vs H-D.P. method, the pressure, P3', may be found directly from polynomial coefficients. For example, if a second-order polynomial is fitted to the pulse amplitude vs H-D.P. data, with coefficients $a_0$, $a_1$, $a_2$, then P3' is given by $$P3' = -a_1/2a_2 \quad (4)$$

This corresponds to the maximum of the polynomial. Similar expressions may be used for third and higher-order polynomials.

ARTERY COMPLIANCE - ACCURACY INDEX CALCULATIONS

The accuracy of tonometric methods of the present type for measuring blood pressure is dependent upon the compliance, or stiffness, of the underlying artery; the accuracy of measurement decreasing with increased stiffness of the artery. A measure of the stiffness, or compliance, of the artery may be obtained using information contained in the diastolic (or systolic) pressure curve 140 and the pulse amplitude curve 142 of FIG. 6. In particular, a measure of compliance of the artery is provided by the ratio of the slope, S2, of the diastolic (or systolic) pressure curve at the correct hold-down pressure P3, and the slope, S1, thereof betewen zero and hold-down pressure P1.

From the above, it will be seen that a measure of compliance, C, of the underlying artery is $$C = S2/S1 \quad (5)$$

As noted above, pressures P1' and P2', equal to 0.6 of the maximum pulse amplitude value of graph 142, substantially correspond to hold-down pressures P1 and P2. Slope S1 is determined by fitting a straight line 144 to the measured diastolic versus hold-down pressure points for hold-down pressures less than P1. As noted above, flattening of the underlying artery does not begin until hold-down pressure P1 is reached. Slope S2 at the correct hold-down pressure P3 is readily obtainable using coefficients of the polynomial (equation 1) identifying curve 140. In particular, $$S2 = a_1 - (a_2^2/3a_3) \quad (6)$$

If the measure of compliance, C, is small compared to unity (say C<0.3) the artery stiffness is relatively low, and intraarterial blood pressure will be measured relatively accurately by the present tonometric method. Larger values of C, approaching unity, indicate that the artery stiffness is relatively large, which may lead to relatively inaccurate measurements. The compliance parameter obtained from equation (5) is calculated at step 119 after the polynomials for the systolic, diastolic and pulse amplitude versus hold-down pressure curves are determined, and the calculated compliance parameter value is stored for display at step 124. The value itself may be displayed, or indications that accuracy is "good", "fair", "poor", or the like, may be displayed, dependent upon the calculated value.

Reference now is made to the flow chart of FIG. 7 wherein details of step 116 of FIG. 5A for computing hold-down pressure are shown. As noted above, when decision step 112 of FIG. 5A is affirmative, indicating that the selected transducer element is near the center of the transducer array, the correct hold-down pressure is computed at step 116. As seen in FIG. 7, this step (step 116) includes waiting for the next heartbeat at step 150, following which the centered transducer element is selected at step 152. At step 154 systolic and diastolic pressures are determined from the blood pressure measurements obtained from the selected transducer element, or rider, and the systolic and diastolic pressure values, along with the hold-down pressure employed, are stored in computer memory 62A. It will be recalled that at stop 104 (FIG. 5A) a nominal hold-down pressure of approximately 120 mmHg was applied. Therefore, the first systolic and diastolic pressure values are obtained using the nominal, 120 mmHg, hold-down pressure.

At step 156 the hold-down pressure is increased by an incremental amount of, say, 5 mmHg. Decision step 158 is then entered to determine whether or not the hold-down pressure is greater than, say, 300 mmHg. If the answer is negative, step 150 is reentered whereupon another set of systolyc and diastolic pressures are obtained and stored for this larger hold-down pressure.

After an entire set of systolic and diastolic pressure values have been obtained for a range of hold-down pressures between 120 and 300 mmHg, decision step 158 is affirmative and step 160 is entered wherein a set of pulse amplitude values are calculated by subtraction of diastolic pressure from the associated systolic pressure value. The pulse amplitude values are stored im memory along with the set of systolic and diastolic pressure values.

At step 162, a polynomial fit (typically a third-order fit) is computed for each of the systolic, diastolic and pulse amplitude versus hold-down pressure sets of data obtained at steps 154 and 160. The shape of curve 140 in FIG. 6 is representative of the shape obtained for both diastolic and systolic pressure vs hold down pressure plots, and curve 142 in FIG. 6 has a shape that is representative of pulse amplitude versus hold-down pressure plots. The constants and coefficients of the polynomials obtained at step 162 are stored for use in step 164 where a correct hold-down pressure is calculated for each polynomial.

As described above, the correct hold-down pressure using the systolic and diastolic versus hold-down pressure points is obtained using equation (2) which locates the point of minimum slope of the plot of the third-order polynomial fitted to the points. In particular, the hold-down pressure is taken as the negative of the coefficient of the second degree term divided by three times the coefficient of the third degree term of the polynomial.

Using the set the pulse amplitude vs hold-down pressure points, the correct hold-down pressure is determined by first calculating a pulse amplitude value substantially equal to sixty percent of maximum pulse amplitude on the graph of the polynomial fitted to th points. The two hold-down pressure values along the graph at which the pulse amplitude values are substantially equal to said sixty percent of maximum pulse amplitude are identified, and the mean value of these two hold-down pressure values is taken as the correct hold-down pressure. Alternatively, the maximum of the polynomial may be determined directly from the polynomial coefficients, which maximum value is taken as the correct hold-down pressure.

At decision step 166 the three (or four) hold-down pressure values calculated in step 164 are compared to determine if the values substantially agree, e.g., if they agree within, say, 10 mmHg of each other. If the correct hold-down values do substantailly agree, the decision is affirmative and step 118 (FIG. 5A) is entered where the hold-down pressure is set within the range of computed values. If they do not substantially agree, the hold-down pressure is reduced to a low value, say 120 mmHg, at step 168 and step 150 is reentered for redetermination of a correct hold-down pressure value.

Although the operation of the blood-pressure monitoring system is believed to be apparent from the above-description, a brief description thereof now will be provided. After turning on or resetting the system (step 100) information regarding the subject is entered into computer memory 62A through keyboard 64 (step 102). A hold-down pressure of approximately 120 mmHg is supplied to the transducer through tube 20 from pressure source 58 (step 104) after which the transducer is attached to the subject (step 106). Outputs from the transducer elements 22A through 22J are digitized at analog to digital converter 60 and are supplied to digital computer 62 for processing. Using outputs from each of the transducer elements 22A through 22J, the transducer element that is substantially centered over the underlying artery is selected as that element from which blood pressure measurements are to be obtained (step 108). A method of selecting the centered transducer element employing analog circuitry is shown in U.S. Pat. No. 4,269,193, which method is readily implemented digitally using digital computer 62. The location of the selected transducer element is displayed (step 110) and if the selected element is not near the center of the array, the array may be repositioned (steps 112 and 114) and the process of selecting the centered element is repeated.

With the transducer properly positioned on the subject, the correct hold-down pressure to employ for obtaining accurate blood pressure measurements is determined (step 106). Four different methods of computing the correct hold-down pressure are disclosed, one or more of which may be employed in a monitoring system. The first, second, and third methods use systolic pressure, diastolic pressure, and pulse amplitude versus hold-down pressure measurements, respectively, which are obtained over hold-down pressures which range from a pressure where the underlying artery is unflattened to a pressure where it is occluded. The fourth method is a variation of the third, using a formula of polynomial coefficients rather than the aforementioned 60% points.

After a heartbeat (step 150, FIG. 7) the transducer element centered over the underlying artery is selected (step 152) and stystolic and diastolic pressures are determined from the blood pressure waveform (FIG. 4) from the selected transducer element. These maximum and minimum pressure points are readily determined by digital computer 62 using known programming methods. The systolic and diastolic pressures are stored in computer memory 62A together with the associated hold-down pressure. The hold-down pressure then is increased an incremental amount (say by 5 mmHg) at step 156, and, if the hold-down pressure is less than about 300 mmHg, the systolic and diastolic pressure values for the new hold-down pressure are obtained and stored for computer memory 62A. If the hold-down pressure is greater than 300 mmHg (step 158), which is a pressure greater than that required for occlusion of the underlying artery, the acquisition of systolic and diastolic pressures versus hold-down pressure values is stopped, and pulse amplitudes for the collected data are calculated and stored. As seen in FIG. 4, pulse amplitude simply comprises the difference in systolic and diastolic pressures for a given cycle of the blood pressure waveform.

Third order polynomials using a least squares method, for example, are fitted to the systolic, diastolic and pulse amplitude versus hold-down pressure values (step 162). From these curves, correct hold-down pressures are calculated (step 164). From the systolic and diastolic pressure curves, the point of minimum slope is determined to provide an indication of correct hold-down pressure. This minimum slope point is located substantially midway between hold-down pressures at which flattening of the underlying artery begins, and at which the artery is occluded. From the pulse amplitude curve, hold-down pressure values at which the pulse amplitude is sixty percent of maximum are determined, which values substantially equal hold-down pressure at which flattening of the underlying artery begins and at which the artery is occluded. Hold-down pressure at the midpoint between the two sixty percent points is taken as the point at which the hold-down pressure is correct. Also, correct hold-down pressure is determined from coefficients of the polynomial fitted to the pulse amplitude values using, for example, equation (4).

If the plurality of "correct" hold-down pressures calculated at step 164 to within, say, 10 mmHg, then the hold-down pressure is set at a value within the calculated range of values (step 118) and an indication that blood pressure readings now are valid is provided at step 120. The blood pressure waveform from the selected transducer element may be displayed or recorded (step 124), and the systolic and diastolic pressures, as well as pulse amplitude and pulse rate may be obtained from the blood pressure waveform (step 122) and displayed at step 124.

At the next heartbeat (step 126), the elapsed time of operation is compared to a predetermined time period, M, such as 30 minutes, and if M minutes have not elapsed, the process of selecting the central transducer element is performed (step 132). If there is a change in the selected transducer element from that which was last-determined, the newly selected element is displayed (step 136) and a warning issued (step 138). The transducer may be repositioned in response to the warning, or the monitoring process may be continued without repositioning of the transducer, but using the newly-selected transducer element. If, at step 134, there has been no change in the selected transducer element, the monitoring process continues without issuance of a warning.

If, at decision step 128, the response is affirmative indicating that M minutes have elapsed, the timer is reset at step 130, the hold-down pressure is decreased to substantially 120 mmHg at step 131, and correct hold-down pressure to be used is recomputed by reentry into step 116.

At step 119 an accuracy index may be calculated, which then is displayed at step 124. The accuracy index is taken at the ratio of the slope of the systolic (or diastolic) pressure versus hold-down curve where the slope is minimum, to the slope of a straight line fitted to the curve before flattening of the artery begins. The minimum slope of the curve is readily determined from coefficients of the polynomial fitted to the curve, and the slope of the straight line is determined by fitting a straight line to the initial portion of the curve. The hold-down pressure $P1'$ at which flattening of the underlying artery begins is determined from the lower sixty percent of maximum pulse amplitude point of the pulse amplitude versus hold-down pressure curve 142.

The invention having been described in detail in accordance with requirements of the Patent Statutes, various other changes and modifications will suggest themselves to those skilled in the art. For example, not all four of the above-described methods of determining correct hold-down pressure need be employed since the four methods generally result in hold-down pressures that are substantially the same. If only one of the methods is employed, then steps 166 and 168 of FIG. 7 would be eliminated from the process. Also, once the transducer is properly positioned and the correct hold-down pressure determined and applied to the transducer, then the waveform from the selected transducer element may be displayed, recorded, or the like, and/or any desired value derived therefrom may be displayed, recorded, or the like. Any desired use may be made of the blood pressure waveform, the invention not being limited to any particular use. Also, analog circuit means may be employed for processing the blood pressure waveform in place of the illustrated digital processing means. Finally, transducers of various constructions (including single-element transducers, capacitive, fiber-optic, piezoresistive and other types of force or pressure transducers) may be used to obtain pressure waveforms from the subject. It is intended that the above and other such changes and modifications shall fall within the spirit and scope of the invention defined in the appended claims.

I claim:

1. A machine implemented method for determining correct hold-down pressure to be applied to an external pressure transducer that includes a pressure sensitive element applied to a subject at a location overlying an artery, the determined correct hold-down pressure identifying the hold-down pressure to be employed to obtain correct blood pressure measurements using said transducer, said method comprising,
    (1) obtaining a continuous measurement of blood pressure with the external pressure transducer while changing the hold-down pressure on the transducer over a range from where the underlying artery is substantially unflattened to where the artery is substantially occluded,
    (2) obtaining from the blood pressure measurement of step 1 a set of at least one of the diastolic pressure, systolic pressure, and pulse amplitude values versus hold-down pressure over said range of hold-down pressures,
    (3) fitting a polynomial to at least one set of values obtained in step 2,
    (4) using the polynomial obtained in step 3, obtaining an indication of the correct hold-down pressure required for accurate blood pressure measurements, and (5) setting the transducer hold-down pressure at substantially the indicated correct hold-down pressure obtained in step 4 in preparation for obtaining accurate blood pressure measurements from said transducer.

2. A method as defined in claim 1 wherein a set of diastolic pressure versus hold-down pressure values are obtained in step 2, and in step 3 a polynomial of at least third-order is fitted to the set of diastolic pressure versus hold-down pressure values.

3. A method as defined in claim 2 wherein step 4 includes locating the point of minimum slope of the graph of the polynomial fitted in step 3 using coefficients of the polynomial, the hold-down pressure at the point of minimum slope providing an indication of the correct hold-down pressure.

4. A method as defined in claim 1 wherein a set of systolic pressure versus hold-down pressure values are obtained in step 2, and in step 3 a polynomial of at least third-order is fitted to the set of systolic pressure versus hold-down pressure values.

5. A method as defined in claim 4 wherein step 4 includes locating the point of minimum slope of the graph of the polynomial fitted in step 3 using coefficients of the polynomial, the hold-down pressure at the point of minimum slope providing an indication of the correct hold-down pressure.

6. A method as defined in claim 1 wherein a set of pulse amplitude versus hold-down pressure values are obtained in step 2, and in step 3 a polynomial of at least second-order is fitted to the set of pulse amplitude versus hold-down pressure values.

7. A method as defined in claim 6 wherein step 4 includes locating a pair of hold-down pressure points at which pulse amplitude is substantially sixty percent of maximum pulse amplitude of the graph of the polynomial, the hold-down pressure at substantially the midpoint of said pair of hold-down pressure points providing an indication of the correct hold-down pressure.

8. A method as defined in claim 6 wherein step 4 includes locating the point of maximum pulse amplitude on the graph of the polynomial fitted in step 3 using coefficients of the polynomial, the hold-down pressure at the point of maximum pulse amplitude providing an indication of the correct hold-down pressure.

9. A blood pressure monitoring system for the continuous external measurements of blood pressure in an underlying artery comprising,
an external pressure transducer applied to a subject at a location overlying an artery, said pressure transducer including a pressure sensitive element having at least one dimension smaller than the lumen of the underlying artery in which blood pressure is measured and substantially centrally positioned over the underlying artery, said pressure sensitive element producing a continuous waveform having an amplitude which is a function of blood pressure in the underlying artery,
means for applying a variable hold-down pressure to the transducer, the hold-down pressure being variable over a range of at least from where the underlying artery is substantially unflattened to where the artery is substantially occluded,
means responsive to the waveform for obtaining a set of at least one of the diastolic pressure, systolic pressure, and pulse amplitude values over a range of hold-down pressures,
means for fitting a polynomial to a set of at least one of the diastolic pressure, systolic pressure, and pulse amplitude versus hold-down pressure values to obtain coefficients of the polynomial,
means employing the polynomial for obtaining an indication of the correct hold-down pressure required for making accurate blood pressure measurements, and
means for maintaining the transducer hold-down pressure at substantially the indicated correct hold-down pressure for obtaining accurate blood pressure measurements from the transducer.

10. A blood pressure monitoring system as defined in claim 9 wherein said means responsive to the waveform comprises means for obtaining a set of diastolic pressure versus hold-down pressure points,
said fitting means includes means for fitting a polynomial of at least a third-order to the set of diastolic versus hold-down pressure points where the polynomial is of the following type:

$$P_m = a_0 + a_1 P_h + a_2 P_h^2 + a_3 P_h^3$$

wherein:
$P_m$ = measured diastolic pressure,
$P_h$ = hold-down pressure, and
$a_0, a_1, a_2,$ and $a_3$ are coefficients of the polynomial, and,
said means for obtaining an indication of correct hold-down pressure comprises means for locating the hold-down pressure, P3, at the point of minimum slope of the graph of the polynomial in accordance with the following equation;

$$P3 = -a_2/3a_3.$$

11. A blood pressure monitoring system as defined in claim 9 wherein said means responsive to the waveform comprises means for obtaining a set of systolic pressure versus hold-down pressure points,
said fitting means includes means for fitting a polymonial of at least third-order to the set of systolic versus hold-down pressure points where the polynomial is of the following type:

$$P_m = a_0 + a_1 P_h + a_2 P_h^2 + a_3 P_h^3$$

wherein:
$P_m$ = measured systolic pressure,
$P_h$ = hold-down pressure, and
$a_0, a_1, a_2,$ and $1_3$ are coefficients of the polynomial, and,
said means for obtaining an indication of correct hold-down pressure comprises means for locating the hold-down pressure, P3, of the point of minimum slope of the graph of the polynomial in accordance with the following equation;

$$P3 = -a_2/3a_3$$

12. A blood prssure monitoring system as defined in claim 9 wherein said means responsive to the waveform comprises means for obtaining a set of pulse amplitude versus hold-down pressure points,
said fitting means comprises means for fitting a polynomial of at least a second-order to the set of pulse amplitude versus hold-down pressure points, said means for obtaining an indication of the correct hold-down pressure comprises means for locating a pair of hold-down pressure points on a graph of the polynomial at which the pulse amplitude equals substantially sixty percent of maximum pulse amplitude of the graph, the hold-down pressure at substantially the means of said pair of hold-down pressure points comprising the correct hold-down pressure.

13. A blood pressure monitoring system as defined in claim 9 wherein said means responsive to the waveform comprises means for obtaining a set of pulse amplitude versus hold-down pressure points, said fitting means comprises means for fitting a polynomial of at least second order to the set of pulse amplitude versus hold-down pressure points, and said means for obtaining an indication of the correct hold-down pressure comprises means employing coefficients of the polynomial for identifying the hold-down pressure at which pulse amplitude is maximum.

14. A machine-implemented method of obtaining a measure of the compliance of a subject's artery underlying an external pressure transducer that includes a pressure sensitive element applied to the subject using a variable hold-down pressure, the method comprising the steps of, (1) obtaining a continuous measurement of blood pressure with the external pressure transducer while changing the hold-down pressure on the transducer over a range from where the underlying artery is unflattened to where the artery is substantially occluded, (2) obtaining from the blood pressure measurement of step 1 a set of at least one of the diastolic and systolic pressure versus hold-down pressure values over said range of hold-down pressures, (3) fitting a polynomial of at least third-order to a set of values obtained in step 2, (4) determining the slope of a straight line fitted to a sub-set of values obtained in step 2 over a range of hold-down pressures below which flattening of the underlying artery occurs, and (5) determining the minimum slope of the graph of the polynomial fitted to said set of values, the ratio of slopes determined in steps 5 and 4 providing a measure of compliance of the underlying artery.

15. A method as defined in claim 14 wherein step 5 includes using coefficients of the polynomial in determining the minimum slope of the graph of the polynomial fitted to said set of pressure values.

16. A method as defined in claim 15 including (6) obtaining from the blood pressure measurement of step 1 a set of pulse amplitude versus hold-down pressure values over said range of hold-down pressures recited in step 2, (7) fitting a polynomial of at least second-order to said set of pulse amplitude versus hold-down pressure values, (8) identifying the hold-down pressure on a graph of the pulse amplitude versus hold-down pressure polynomial at which the pulse amplitude substantially equals to sixty percent of maximum pulse amplitude of the graph of the pulse amplitude versus hold-down pressure polynomial, and (9) employing the lower hold-down pressure identified in step 8 as the upper end of the range of hold-down pressures used in step 4 for determining the slope of said straight line.

17. A blood pressure monitoring system for continuous external measurement of blood pressure in an underlying artery and for obtaining a measure of compliance of said underlying artery comprising a pressure transducer that includes a pressure sensitive element having at least one dimension smaller than the lumen of the underlying artery and substantially centrally positioned over the artery, said pressure sensitive element producing a continuous waveform having an amplitude which is a function of blood pressure in the underlying artery, means for applying a variable hold-down pressure to the transducer, means responsive to the waveform for obtaining a set of diastolic pressure values, a set of systolic pressure values, and a set of pulse amplitude values over a range of hold-down pressures, means for fitting a polynomial of at least third-order to a set of at least one of the diastolic pressure and systolic pressure versus hold-down pressure values and for fitting a polynomial of at least second-order to said pulse amplitude versus hold-down pressure values, means for identifying the lowest hold-down pressure at which the pulse amplitude substantially equals sixty percent of the maximum pulse amplitude on the graph of the pulse amplitude versus hold-down pressure polynomial, means for determining the slope of a straight line fitted to a sub-set of at least one of the diastolic pressure and systolic pressure values over a range of hold-down pressures below said hold-down pressure identified as the lowest hold-down pressure at which the pulse amplitude substantially equals sixty percent of the maximum, and means for determining the minimum slope of the graph of at least one of the polynomials of diastolic pressure and systolic pressure versus hold-down pressure values, the ratio of said minimum slope to the slope of said straight line providing a measure of compliance of the underlying artery.

18. A system as defined in claim 17 including means for setting the hold-down pressure of the transducer at substantially the hold-down pressure at which the slope of at least one of the graphs of the diastolic pressure and systolic pressure versus hold-down pressure polynomial is minimum.

19. A system as defined in claim 17 including means for setting the hold-down pressure of the transducer at substantially the hold-down pressure midway between the pair of hold-down pressures at which the pulse amplitude polynomial substantially equals sixty percent of the maximum pulse amplitude on the graph of the pulse amplitude versus hold-down pressure polynomial.

20. A system as defined in claim 17 including means for setting the hold-down pressure of the transducer at substantially the hold-down pressure at which the pulse amplitude polynomial is maximum.

* * * * *